US008258318B2

(12) United States Patent
Suzuki et al.

(10) Patent No.: US 8,258,318 B2
(45) Date of Patent: Sep. 4, 2012

(54) PROCESS FOR PRODUCTION OF COUMARIN DIMER COMPOUND

(75) Inventors: Hideo Suzuki, Funabashi (JP); Takayuki Tamura, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 261 days.

(21) Appl. No.: 12/451,213

(22) PCT Filed: Apr. 28, 2008

(86) PCT No.: PCT/JP2008/058198
§ 371 (c)(1),
(2), (4) Date: Oct. 30, 2009

(87) PCT Pub. No.: WO2008/136460
PCT Pub. Date: Nov. 13, 2008

(65) Prior Publication Data
US 2010/0130755 A1 May 27, 2010

(30) Foreign Application Priority Data

May 2, 2007 (JP) ................................ 2007-121683

(51) Int. Cl.
*C07D 311/00* (2006.01)
(52) U.S. Cl. ...................................... 549/275
(58) Field of Classification Search ................ 549/275
See application file for complete search history.

(56) References Cited

OTHER PUBLICATIONS

Hartner et al. Journal of Photochemistry and Photobiology A: Chemistry 187, 2007, 242-246.*
Chen et al. Polymer Science Part A: Polymer Chemistry 35, 1997, 613-624.*
Ho et al. teach Patai's Chemistry of Functional Groups, Online 2009 John Wiley & Sons, Ltd. 1-75, see pp. 1-2.*
Dorwald F. A. Side Reactions in Organic Synthesis, 2005, Wiley: VCH, Weinheim p. IX of Preface p. 1-15.*
Hasegawa et al., (Photochemistry and Photophysics, 1990, Chapter 2, see Sections under Reactions with Nucleophiles and Concluding Remarks.*
Schenck et al., "Photosensibilisierte Cyclodimerisation von Cumarin," 1962, vol. 95, pp. 1409-1412.
Chen et al., "Synthesis and Reversible Photocleavage of Novel Polyurethanes Containing Coumarin Dimer Components," *Journal of Polymer Science, Part A: Polymer Chemistry*, 1997 vol. 35, pp. 613-624.
D'Auria et al., "The photodimerisation of coumarin," *Journal of Photochemistry and Photobiology A: Chemistry*, 2004, vol. 163, pp. 557-559.
Morrison et al., "Solvent Effects on the Photodimerization of Coumarin," *Journal of the American Chemical Society*, 1966, vol. 88, No. 23, pp. 5415-5419.
Yu et al., "Selectivity in the Photodimerization of 6-Alkylcoumarins," *J. Org. Chem.*, 2003, vol. 68, pp. 7386-7399.
Hartner et al., "Photodimerized 7-hydrxoycoumarin with improved solubility in PMMA: Single-photon and two-photon-induced photocleavage in solution and PMMA films," *Journal of Photochemistry and Photobiology A: Chemistry*, 2007 vol. 187, pp. 242-246.
International Search Report issued in International Application No. PCT/JP2008/058198 on Jun. 17, 2008 (with English-language translation).

* cited by examiner

*Primary Examiner* — Nizal Chandrakumar
(74) *Attorney, Agent, or Firm* — Oliff & Berridge, PLC

(57) ABSTRACT

There is provided a one-step process for producing a dihydroxy-substituted coumarin dimer compound by a photodimerization reaction of a hydroxy-substituted coumarin compound. The process comprises subjecting a hydroxy-substituted coumarin compound to a photodimerization reaction in a solvent selected from aliphatic ketones having 3 to 10 carbon atoms, aliphatic carboxylic acid esters having 2 to 10 carbon atoms, aliphatic alcohols having 1 to 10 carbon atoms, aliphatic nitriles having 2 to 10 carbon atoms, ethers having 4 to 10 carbon atoms, amides having 3 to 10 carbon atoms, and a mixture thereof to obtain a dihydroxy-substituted coumarin dimer compound.

6 Claims, 1 Drawing Sheet

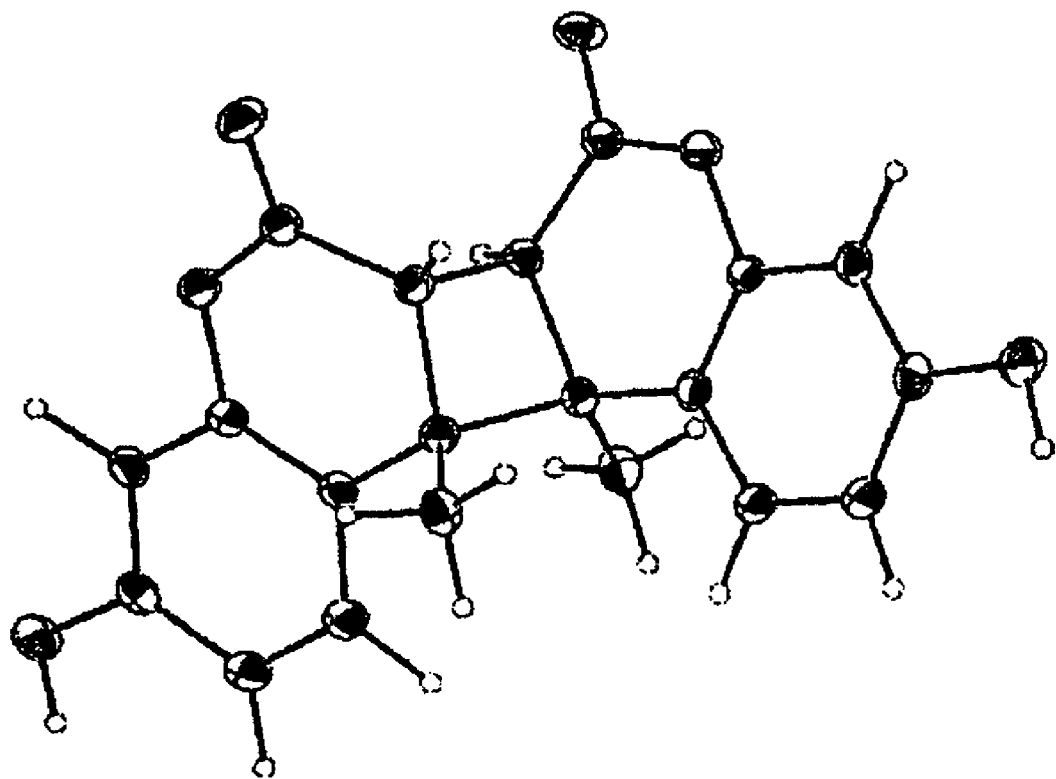

PROCESS FOR PRODUCTION OF COUMARIN DIMER COMPOUND

TECHNICAL FIELD

The present invention relates to a process for producing a coumarin dimer compound. In more detail, the present invention relates to a process for producing a dimer of a coumarin compound substituted with a hydroxy group.

BACKGROUND ART

A process for producing an unsubstituted coumarin dimer compound by subjecting unsubstituted coumarin to a photodimerization reaction is conventionally known. For example, Non-patent Document 1 describes an example for effecting a photodimerization reaction using benzene as a solvent, and benzophenone as a sensitizer.

Meanwhile, as a process for producing a hydroxy-substituted coumarin compound dimer compound, there has been developed a production process including: acetylating a hydroxy-substituted coumarin compound with acetic anhydride; obtaining a bis-acetoxy-substituted coumarin dimer compound through a photodimerization reaction; hydrolyzing the dimer compound with an aqueous mixture of an aqueous hydrochloric acid solution and ethanol; and extracting the hydrolyzed dimer compound with ethyl acetate and refluxing the extracted dimer compound with an acetic acid to isolate the objective dihydroxy-substituted coumarin dimer compound (Non-patent Document 2).

[Non-patent Document 1]
G. O. Schenck et. al. "Chemische Berichte" Germany, 1962, Vol. 95, pp. 1409-1412

[Non-patent Document 2]
Y. Chen et. al. "Journal of Polymer Science: Part A: Polymer Chemistry" 35, 613-624 (1997)

DISCLOSURE OF THE INVENTION

Problems to be Solved by the Invention

As a process for producing a hydroxy-substituted coumarin dimer compound, the production process described in Non-patent Document 2 is disadvantageous in terms of production efficiency because of requiring four steps. Furthermore, the process cannot be regarded as a preferred production process from the viewpoint of economy and green chemistry because of using indirect materials such as acetic anhydride, hydrochloric acid, ethanol, ethyl acetate and acetic acid, which are not directly involved in the structure of an objective product. Therefore, a new production process taking these problems into consideration has been required.

On the other hand, by the photodimerization method under a condition of using benzene (solvent) and benzophenone (sensitizer) which is described in Non-patent Document 1, although the photodimerization of an unsubstituted coumarin compound can be achieved, a hydroxy-substituted coumarin dimer compound cannot be obtained.

In order to solve the problems described above, it is an object of the present invention to provide a one-step process for producing a dihydroxy-substituted coumarin dimer compound by a photodimerization reaction of a hydroxy-substituted coumarin compound.

Means for Solving the Problems

The present inventors have made extensive and intensive studies in order to solve the above problems. As a result, it has been found that a dihydroxy-substituted coumarin dimer compound can be produced through one step by selecting specific reaction conditions in a photodimerization reaction of a hydroxy-substituted coumarin compound. Based on this finding, the present invention has been completed.

Namely, the present invention relates to, according to a first aspect, a process for producing a coumarin dimer compound characterized by including: obtaining coumarin dimer compounds represented by Formula (2) and Formula (3):

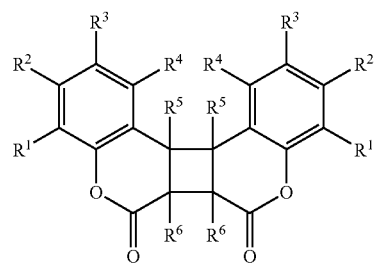

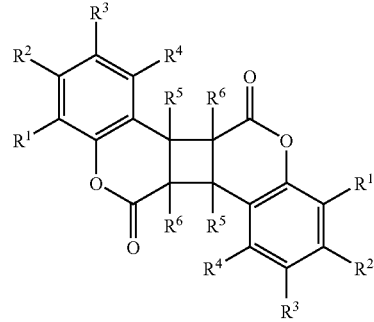

(where $R^1$, $R^2$, $R^3$, $R^4$, $R^5$ and $R^6$ independently represent a hydrogen atom, an alkyl group having 1 to 10 carbon atoms, a halogen atom, a nitro group, an amino group, a cyano group, a carboxy group, an alkoxycarbonyl group having 1 to 10 carbon atoms, a halogenated alkyl group having 1 to 10 carbon atoms, or a hydroxy group; and at least one of $R^1$ to $R^6$ represents a hydroxy group), by subjecting a coumarin compound represented by Formula (1):

[1]

(where $R^1$, $R^2$, $R^3$, $R^4$, $R^5$ and $R^6$ represent the same meaning as defined above),
to a photodimerization reaction in a solvent selected from aliphatic ketones having 3 to 10 carbon atoms, aliphatic carboxylic acid esters having 2 to 10 carbon atoms, aliphatic alcohols having 1 to 10 carbon atoms, aliphatic nitriles having 2 to 10 carbon atoms, ethers having 4 to 10 carbon atoms, amides having 3 to 10 carbon atoms, and a mixture thereof.

The present invention relates to, according to a second aspect, the process for producing a coumarin dimer compound according to the first aspect, characterized in that the solvent is aliphatic ketones.

The present invention relates to, according to a third aspect, the process for producing a coumarin dimer compound according to the first aspect or the second aspect, characterized in that the photodimerization reaction is effected in the presence of a photosensitizer.

The present invention relates to, according to a fourth aspect, the process for producing a coumarin dimer compound according to any one of the first aspect to the third aspect, characterized in that a high-pressure mercury lamp is used as a light source used for the photodimerization reaction.

The present invention relates to, according to a fifth aspect, the process for producing a coumarin dimer compound according to any one of the first aspect to the fourth aspect, characterized in that the photodimerization reaction is effected in a reactor equipped with a light source-cooling tube that is made of glass and absorbs light having a wavelength of 300 nm or less.

The present invention relates to, according to a sixth aspect, the process for producing a coumarin dimer compound according to any one of the first aspect to the fifth aspect, characterized in that the production process is performed at a reaction temperature of −50° C. to 80° C.

Effects of the Invention

By the production process of the present invention, a dihydroxy-substituted coumarin dimer compound can be produced through one step, and a production process that is excellent in economical efficiency and environmental efficiency and has high practicability can be provided.

BEST MODES FOR CARRYING OUT THE INVENTION

The present invention will be described in more detail.

The process for producing a dihydroxy-substituted coumarin dimer compound of the present invention is represented by the following reaction scheme.

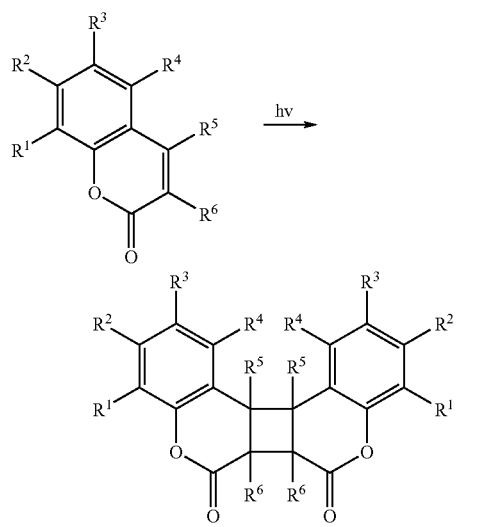

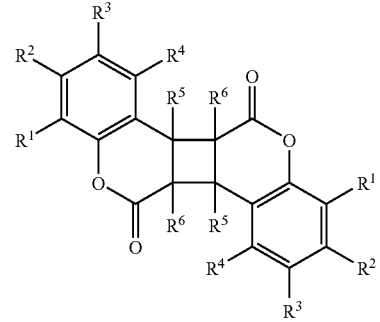

(where $R^1$, $R^2$, $R^3$, $R^4$, $R^5$ and $R^6$ represent a hydrogen atom, an alkyl group having 1 to 10 carbon atoms, a halogen atom, a nitro group, an amino group, a cyano group, a carboxy group, an alkoxycarbonyl group having 1 to 10 carbon atoms, a halogenated alkyl group having 1 to 10 carbon atoms, or a hydroxy group; and one or more of $R^1$ to $R^6$ represent(s) a hydroxy group.)

Specific examples of the hydroxy-substituted coumarin compound used in the production process of the present invention include the following compounds.

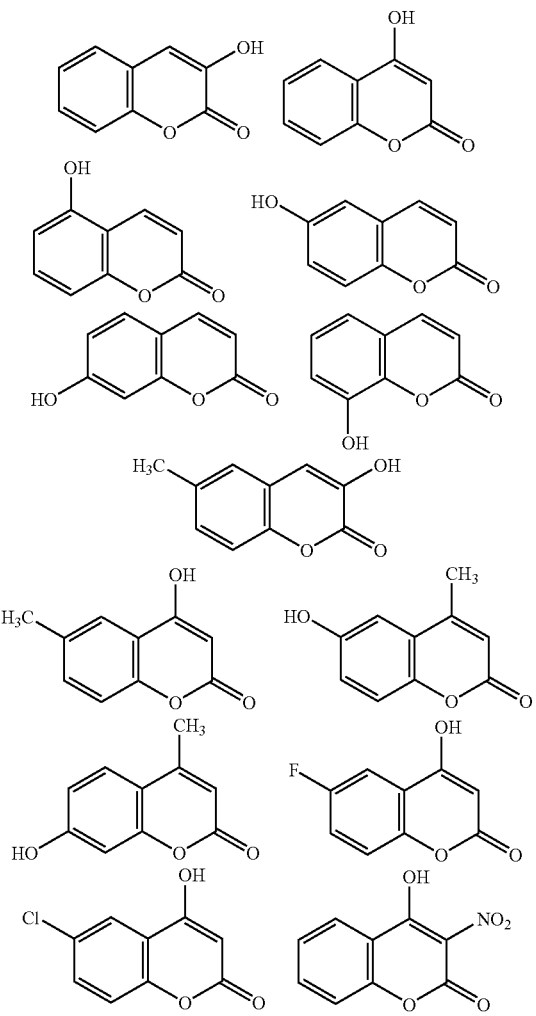

-continued

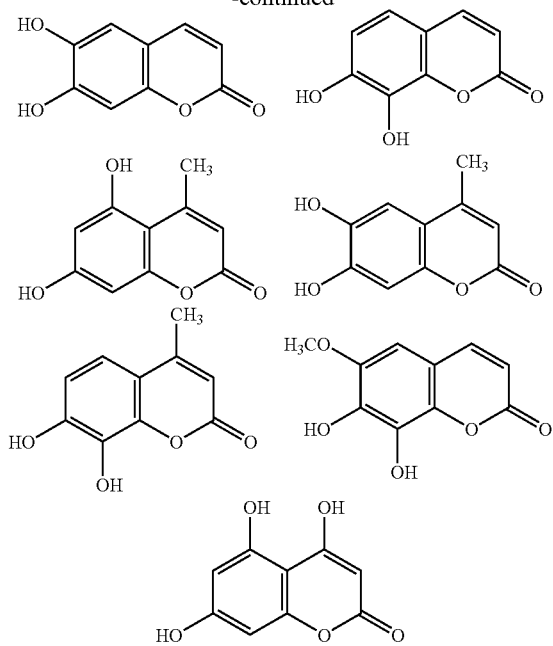

Examples of the solvent used in the production process of the present invention include aliphatic ketones having 3 to 10 carbon atoms, aliphatic carboxylic acid esters having 2 to 10 carbon atoms, aliphatic alcohols having 1 to 10 carbon atoms, aliphatic nitriles having 2 to 10 carbon atoms, ethers having 4 to 10 carbon atoms and amides having 3 to 10 carbon atoms.

Specific examples of the above solvent include the followings.

(a) aliphatic ketones having 3 to 10 carbon atoms: acetone, methyl ethyl ketone, methyl n-propyl ketone, methyl isopropyl ketone, methyl n-butyl ketone, methyl isobutyl ketone, diethyl ketone, diisopropyl ketone, diisobutyl ketone, cyclohexanone and the like.

(b) aliphatic carboxylic acid esters having 2 to 10 carbon atoms: methyl formate, ethyl formate, n-propyl formate, isopropyl formate, isobutyl formate, methyl acetate, ethyl acetate, n-propyl acetate, isopropyl acetate, isobutyl acetate, methyl propionate, ethyl propionate, n-propyl propionate, isopropyl propionate, ethylene glycol diformate, ethylene glycol diacetate, ethylene glycol dipropionate and the like.

(c) aliphatic alcohols having 1 to 10 carbon atoms: methanol, ethanol, n-propanol, isopropanol, n-butanol, isobutanol, s-butanol, 1-pentanol, 2-pentanol, 3-pentanol, 1-hexanol, 2-hexanol, 3-hexanol, cyclohexanol and the like.

(d) aliphatic nitriles having 2 to 10 carbon atoms: acetonitrile, propionitrile, butylonitrile, valeronitrile and the like.

(e) ethers having 4 to 10 carbon atoms: diethyl ether, di-n-propyl ether, diisopropyl ether, di-n-butyl ether, di-isobutyl ether, di-n-pentyl ether, diisopentyl ether, tetrahydrofuran (THF), 1,3-dioxane, 1,4-dioxane and the like.

(f) amides having 3 to 10 carbon atoms: N,N-dimethylformamide, N,N-dimethylacetamide, N,N-diethylformamide, N,N-diethylacetoamide, N-methyl-2-pyrrolidinone, 1,3-dimethyl-2-imidazolidinone and the like.

Among them, more preferred solvents are aliphatic ketones having 3 to 10 carbon atoms and the most preferred solvent is acetone.

The amount used of the solvent is 5 to 200 parts by mass, preferably 10 to 100 parts by mass, relative to 1 part by mass of a coumarin compound represented by Formula (1).

The production process of the present invention is characterized in that a photodimerization reaction is effected in the presence of a photosensitizer.

Preferred examples of the photosensitizer include aromatic ketones such as benzophenone and acetophenone.

The amount used of the photosensitizer is 0.1 to 50% by mass, more preferably 1 to 30% by mass, based on the mass of the coumarin compound represented by Formula (1).

Here, in the production process of the present invention, when a carbonyl-based compound (ketones, carboxylic acid esters) is used as the solvent, the photodimerization reaction may be progressed without using a photosensitizer.

Examples of the light source used for the photodimerization reaction include a low-pressure mercury lamp (internal irradiation), a high-pressure mercury lamp (internal irradiation), an ultra-high pressure mercury lamp (external irradiation) and a xenon lamp (external irradiation). Among them, the high-pressure mercury lamp is most preferred.

This is because, according to the production process of the present invention, it is considered that a wavelength in a region of 300 nm or less is involved with a polymer formation or a reverse reaction, and that it is preferred to irradiate light having a wavelength of 300 to 600 nm in the formation of a dimer.

In other words, the low-pressure mercury lamp has a high-strength light emission spectrum at around 254 nm and when the low-pressure mercury lamp is used as the light source, a photo-polymerization reaction is progressed rather than a photo-dimerization reaction. On the other hand, when the ultra-high pressure mercury lamp or the xenon lamp is used as the light source, the lamp is an external light source, so that the light efficiency becomes impaired.

Accordingly, by adopting the high-pressure mercury lamp as the light source, the objective dimer compound can be specifically obtained with a high yield.

In addition, by using as a light source-cooling tube that houses the above light source, a glass tube that absorbs light having a wavelength of 300 nm or less, not only a polymer formation can be prevented, but also the attachment of a colored polymer to the light source-cooling tube can be reduced. Therefore, the lowering of the light efficiency can be suppressed. Thus, the yield of the objective dimer compound can be improved.

Here, examples of the glass that absorbs light having a wavelength of 300 nm or less include Pyrex (registered trade mark).

In the production process of the present invention, the reaction is effected preferably at a reaction temperature of −50 to 80° C. When the reaction temperature is higher, by-products such as polymers or decomposition products are produced and when the reaction temperature is lower, the solubility of a raw material is lowered and the production efficiency is lowered. More preferably, by performing the production at −40 to 50° C., the formation of by-products is largely suppressed, so that the objective dimer compound can be obtained with high selectivity and high yield.

In addition, the reaction time (light irradiation time) can be selected from 1 to 50 hours and generally, a reaction time of 5 to 20 hours is practical.

In the production process of the present invention, the photodimerization reaction can be effected by any method of a batch method or a flow method, and at a normal pressure or under pressure.

After the completion of the photodimerization reaction, by concentrating the reaction solution to distil off the solvent and recrystallizing the concentrated reaction solution in ethyl acetate, n-heptane, and the like, the objective dimer compound can be obtained.

EXAMPLES

The present invention will be described more specifically referring to examples, which should not be construed as limiting the scope of the present invention.

In each example, the apparatus and conditions for measuring each physical property are as follows.

[1: Mass Spectrometry (MASS)]
Measuring apparatus: JMS LX 1000 (manufactured by JEOL Ltd.)
Detection method: ionization method: DEP (EI$^+$) m/z=50 to 1,000

[2: $^1$H-NMR]
Measuring apparatus: JNM-LA400 FT-NMR system (manufactured by JEOL Ltd.)
Measuring solvent: DMSO-d$_6$

[3: $^{13}$C-NMR]
Measuring apparatus: JNM-LA400 FT-NMR system (manufactured by JEOL Ltd.)
Measuring solvent: DMSO-d$_6$

[4: Melting Point (mp.)]
Measuring apparatus: Full-automatic melting point measuring apparatus FP62 (manufactured by Mettler-Toledo International Inc.)

[5: X-Ray Structure Analysis]
Measuring apparatus: DIP2030 (manufactured by MAC Science Company, Limited)
X-ray: MoKα (40 kV, 200 mA)
Measuring temperature: room temperature
Sample: Plate-shaped crystal (0.4×0.2×0.05 mm)

[6: Liquid Chromatography]
Measuring apparatus: SHIMADSU SCL-10A vp (manufactured by Shimadzu Corporation)
Column: Inertsil (registered trademark) ODS-3 (5 μm, 4.6×250 mm) (manufactured by GL Sciences Inc.)
Mobile phase: MeCN/H$_2$O=60/40 (v/v)
Flow rate: 1.0 mL/min
Column temperature: 40° C.
Detection: ultraviolet rays (UV) 254 nm
Injection rate: 10 μL Example 1

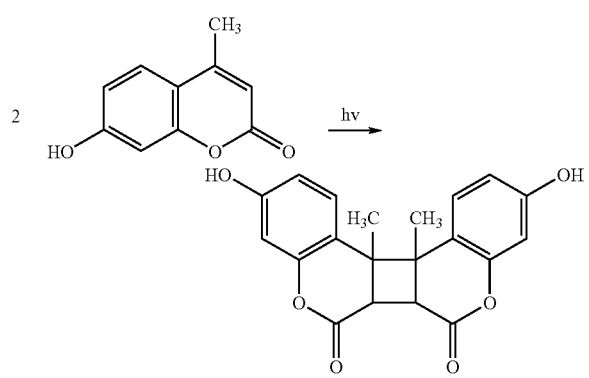

Into an internal irradiation-type (for irradiating UV rays, using a high-pressure mercury lamp of 100 W) four-neck reaction flask (capacity: 200 mL, made of Pyrex (registered trademark) glass), 2 g of 7-hydroxy-4-methylcoumarin (7H4MC), 0.3 g (15% by mass, based on the amount used of 7H4MC) of benzophenone and 200 mL of acetone were charged, and while covering the outer wall of the reactor with an aluminum foil, the mixture was stirred to be dissolved at 20° C. Subsequently, while stirring the resultant mixture, light irradiation of a 100 W high-pressure mercury lamp in a light source-cooling tube positioned in the center of the flask was started. The irradiation was continued for 6 hours to effect a photodimerization reaction.

After the irradiation, a part of the reaction solution was sampled to analyze the sample by a liquid chromatography (LC). It was found that the product was produced with 86% by area. Subsequently, the reaction solution was retrieved and concentrated, and then the resultant residue was recrystallized in ethyl acetate and n-heptane to obtain 1.16 g (isolated yield: 58%) of a crystal-shaped product.

A $^1$H-NMR measurement and a MASS measurement of the above product were performed and the product was confirmed to be the objective 7H4MC dimer.

The results of the MASS measurement, $^1$H-NMR measurement and $^{13}$C-NMR measurement of the product and the melting point of the product are shown as follows.

MASS (ES$^-$, m/e (%)): 351 ([M–H]$^-$, 5).
$^1$H-NMR (d$_6$-DMSO, δ ppm): 1.1037 (s, 6H), 3.3896 (s, 2H), 6.4575 (s, 2H), 6.6761 (d, J=2.5 Hz, 2H), 7.1835 (d, J=8.3 Hz, 2H), 9.8526 (s, 2H).
$^{13}$C-NMR (d$_6$-DMSO, δ ppm): 26.2291 (2C), 39.7767 (2C), 40.0534 (2C), 103.1737 (2C), 112.4567 (2C), 113.8115 (2C), 129.0096 (2C), 150.9815 (2C), 157.8125 (2C), 166.1033 (2C).
mp. (° C.): 218-221

In addition, the product was dissolved in methanol/n-heptane of 60° C. and the resultant solution was gradually cooled to a room temperature to produce a single crystal sample, followed by performing an X ray structure analysis of the sample to clarify the stereostructure of the crystal.

This structure was found to be of an anti head-to-head type, which is different from an anti head-to-tail type described in Non-patent Document 2. The stereostructure of the product is shown in FIG. 1 and the crystallographic parameter of the product is as follows.

TABLE 1

| Crystallographic parameter of 7H4MC dimer | |
| --- | --- |
| Molecule Formula | C$_{16}$H$_{20}$O$_6$ |
| Crystal system | Triclinic |
| Space group | P - 1 |
| Lattice constant | a (Å) = 7.178(1) |
|  | b (Å) = 10.819(1) |
|  | c (Å) = 10.818(1) |
|  | α (°) = 77.536(7) |
|  | β (°) = 82.835(8) |
|  | γ (°) = 82.824(8) |
|  | v (Å$^3$) = 809.8(4) |
| Z | 2 |
| R/wR | 0.08/0.12 |

Examples 2 to 6

The photodimerization reaction was effected under substantially the same conditions as in Example 1, except that the type of the solvents and the reaction time (light irradiation time) were changed. The used solvents, the reaction time and the yields of the obtained 7H4MD dimer are shown in Table 2 (here, the result of Example 1 is also shown therein).

Here, the yield (%) of 7H4MC dimer represents an LC % by area of 7H4MC dimer between the raw material (7H4MC) and the product (7H4MC dimer).

TABLE 2

| Example | Solvent | Reaction time (h) | 7H4MC dimer yield (%) |
|---|---|---|---|
| 1 | Acetone | 6 | 86 |
| 2 | Ethyl acetate | 8 | 68 |
| 3 | Acetonitrile | 7 | 55 |
| 4 | Methanol | 8 | 75 |
| 5 | 1,4-dioxane | 8 | 67 |
| 6 | DMF* | 7 | 39 |

*DMF: N,N-dimethylformamide

Comparative Examples 1 to 3

The photodimerization reaction was effected under substantially the same conditions as in Example 1, except that the type of the solvents and the reaction time (light irradiation time) were changed. The used solvents, the reaction time and the yields of the obtained 7H4MD dimer are shown in Table 3.

TABLE 3

| Comparative Example | Solvent | Reaction time (h) | 7H4MC dimer yield (%) |
|---|---|---|---|
| 1 | Benzene | 8 | 0 |
| 2 | Methylene chloride | 8 | 0 |
| 3 | Cyclohexane | 8 | 0 |

Examples 7 to 9

The photodimerization reaction was effected under substantially the same conditions as in Example 1, except that the reaction temperatures and the used solvents (type of ketone) were changed. The used solvents, the reaction temperatures and the yields of the obtained 7H4MD dimer are shown in Table 4.

TABLE 4

| Example | Solvent (ketones) | Reaction temp. (° C.) | 7H4MC dimer yield (%) (isolated yield (%)) |
|---|---|---|---|
| 1 | Acetone | 20 | 86 (58) |
| 7 | Acetone | 5 | 92 |
| 8 | Acetone | −20 | 96 (70) |
| 9 | Methyl isobutyl ketone | 5 | 92 (76) |

Examples 10 and 11

The photodimerization reaction was effected under substantially the same conditions as in Example 7, except that the added amount of benzophenone was changed. The benzophenone concentrations (concentrations relative to the amounts used of 7HMC) and the yields of the obtained 7H4MD dimer are shown in Table 5.

TABLE 5

| Example | Benzophenone concentration (wt %) | 7H4MC dimer yield (%) |
|---|---|---|
| 10 | 0 | 36 |
| 11 | 5 | 91 |
| 7 | 15 | 92 |

Example 12

The photodimerization reaction was effected under substantially the same conditions as in Example 8, except that 16 g of 7H4MC and 2.4 g (15% by mass, based on the amount used of 7H4MC) of benzophenone were used and the light irradiation time was changed to 12 hours.

After the irradiation, a part of the reaction solution was sampled to analyze the sample by a liquid chromatography (LC). It was found that the product was produced with 90% by area. Subsequently, the product was subjected to substantially the same post-treatment as in Example 1, and 12.8 g (yield: 80%) of 7H4MC dimer in a purity of 87% was obtained.

Examples 13 to 15

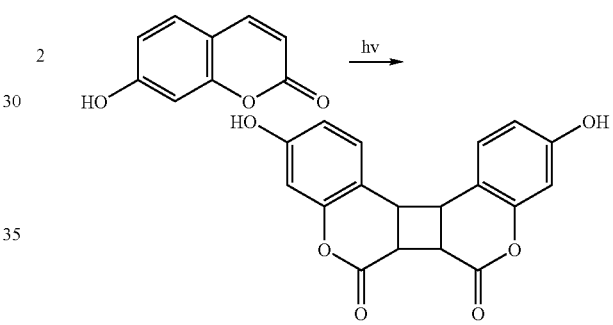

The photodimerization reaction was effected under substantially the same conditions as in Example 1, except that the raw base material was changed to 7-hydroxycoumarin (7HC), and the reaction temperatures and the reaction time (light irradiation time) were changed. The reaction temperatures, the reaction time and the yields of the obtained 7HC dimer are shown in Table 6.

In addition, in Example 14, after the completion of the reaction, the reaction solution was retrieved and concentrated and then the resultant residue was recrystallized in ethyl acetate and n-heptane to obtain 1.28 g (isolated yield: 64%) of a crystal-shaped product.

A $^1$H-NMR measurement and a MASS measurement of the obtained product were performed, and the product was confirmed to be the objective 7HC dimer.

The results of the MASS measurement, $^1$H-NMR measurement and $^{13}$C-NMR measurement of the product and the melting point of the product are shown as follows.

MASS (FAB$^+$, m/e(%)): 322.9 ([M−H]$^-$, 12).

$^1$H-NMR (d$_6$-DMSO, δ ppm): 3.6256 (d, J=7.9 Hz, 2H), 3.8305 (d, J=7.5 Hz, 2H), 6.4595 (d, J=1.7 Hz, 2H), 6.6297 (dd, J$_1$=6.9 Hz, J$_2$=8.3 Hz, 2H), 7.136 (d, J=8.3 Hz, 2H), 9.8183 (s, 2H).

$^{13}$C-NMR (d$_6$-DMSO, δ ppm): 38.7080 (2C), 39.7767 (2C), 100.4736 (2C), 108.8788 (2C), 109.7565 (2C), 126.4620 (2C), 148.3957 (2C), 155.0454 (2C), 163.1263 (2C).

mp. (° C.): 241

TABLE 6

| Example | Reaction temp. (° C.) | Reaction time (h) | 7HC dimer* yield (%) [isolated yield (%)] |
|---|---|---|---|
| 13 | 20 | 20 | 50 |
| 14 | 5 | 14 | 91 (64) |
| 15 | −20 | 6 | 22 |

*The yield (%) of 7HC dimer represents an LC % by area of 7HC dimer between the raw material (7HC) and the product (7HC dimer).

BRIEF DESCRIPTION OF THE DRAWINGS

FIG. 1 shows a stereostructure of the 7H4MC dimer obtained in Example 1, which is obtained by an X-ray structure analysis.

The invention claimed is:

1. A process for producing a coumarin dimer compound, comprising:
obtaining coumarin dimer compounds represented by Formula (2) and Formula (3):

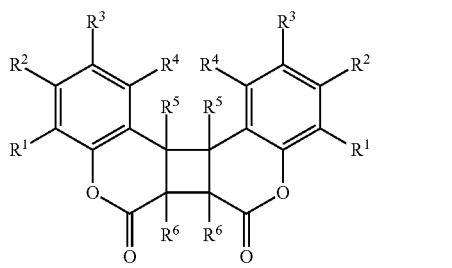

[2]

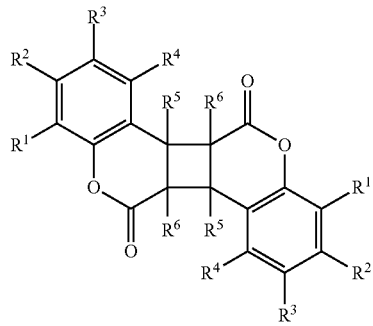

[3]

wherein $R^1$, $R^3$, and $R^4$ independently represent a hydrogen atom, an alkyl group having 1 to 10 carbon atoms, or a halogen atom; $R^2$ represents a hydroxy group; and $R^5$ and $R^6$ independently represent a hydrogen atom or an alkyl group having 1 to 10 carbon atoms,
by subjecting a coumarin compound represented by Formula (1):

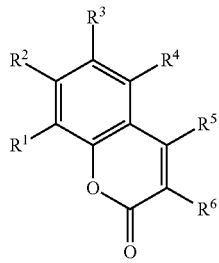

[1]

wherein $R^1$, $R^2$, $R^3$, $R^4$, $R^5$ and $R^6$ represent the same meaning as defined above,
to a photodimerization reaction in a solvent selected from aliphatic ketones having 3 to 10 carbon atoms, aliphatic carboxylic acid esters having 2 to 10 carbon atoms, aliphatic alcohols having 1 to 10 carbon atoms, aliphatic nitriles having 2 to 10 carbon atoms, ethers having 4 to 10 carbon atoms, amides having 3 to 10 carbon atoms.

2. The process for producing a coumarin dimer compound according to claim 1, wherein the solvent is aliphatic ketones.

3. The process for producing a coumarin dimer compound according to claim 1, wherein the photodimerization reaction is effected in the presence of a photo sensitizer.

4. The process for producing a coumarin dimer compound according to claim 1, wherein a high-pressure mercury lamp is used as a light source used for the photodimerization reaction.

5. The process for producing a coumarin dimer compound according to claim 1, wherein the photodimerization reaction is effected in a reactor equipped with a light source-cooling tube that is made of glass and absorbs light having a wavelength of 300 nm or less.

6. The process for producing a coumarin dimer compound according to claim 1, wherein the production process is performed at a reaction temperature of −50° C. to 80° C.

* * * * *